(12) United States Patent
Wolf et al.

(10) Patent No.: US 8,676,543 B2
(45) Date of Patent: Mar. 18, 2014

(54) DETERMINING THE RESONANCE PARAMETERS FOR MECHANICAL OSCILLATORS

(75) Inventors: H. Alan Wolf, Morristown, NJ (US); Chung-Min Cheng, Randolph, NJ (US); George Akehurst, Belvidere, NJ (US); Yvonne Mathez, legal representative, Belvidere, NJ (US); Dalia G. Yablon, Livingston, NJ (US); Alan M. Schilowitz, Highland Park, NJ (US); Manuel S. Alvarez, Warrenton, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 773 days.

(21) Appl. No.: 12/792,500

(22) Filed: Jun. 2, 2010

(65) Prior Publication Data

US 2010/0324852 A1     Dec. 23, 2010

Related U.S. Application Data

(60) Provisional application No. 61/269,329, filed on Jun. 23, 2009.

(51) Int. Cl.
    *H04B 15/00*      (2006.01)
(52) U.S. Cl.
    USPC ............. 702/190; 702/33; 702/57; 702/69; 702/77; 702/191; 702/194; 702/199; 702/189
(58) Field of Classification Search
    USPC ........................................ 702/190
    See application file for complete search history.

(56) References Cited

U.S. PATENT DOCUMENTS

| | | |
|---|---|---|
| 3,253,219 A | 5/1966 | Littler |
| 3,903,732 A | 9/1975 | Rork et al. |
| 4,095,474 A | 6/1978 | Hancock et al. |
| 4,312,228 A | 1/1982 | Wohltjen |
| 4,361,026 A | 11/1982 | Muller et al. |
| 4,412,174 A | 10/1983 | Conlon et al. |
| 4,696,191 A | 9/1987 | Claytor et al. |
| 4,862,384 A | 8/1989 | Bujard |

(Continued)

OTHER PUBLICATIONS

Petersan et al., "Measurement of resonant and quality factor of microwave resonators: comparison of methods," J. of APplie Physics (1998).*

(Continued)

*Primary Examiner* — Jonathan C. Teixeira Moffat
*Assistant Examiner* — Hyun Park
(74) *Attorney, Agent, or Firm* — Ronald D. Hantman

(57) ABSTRACT

Mechanical oscillators employ the use of resonance parameters, frequency and the quality factor Q, for the measurement of corrosion or deposition. The ability of a mechanical oscillator to measure small amounts of metal loss or deposition is not only dependent upon the mechanical design but is limited by the precision in determining the resonance frequency and Q. Methods for measuring these resonance parameters with a high precision in the presence of noise are provided. The increased degree of precision improves the utility of these devices as sensitive probes for corrosion and deposition (fouling) measurement. The increased degree of precision is enabled in part by employing curve fitting consistent with modeling the mechanical oscillator as a simple harmonic oscillator. This curve fitting procedure, combined with averaging and utilizing signal processing parameters to mitigate noise effects, adds precision in measuring resonance parameters.

9 Claims, 14 Drawing Sheets

Mechanical Oscillator with Piezo-Electric Transducer

(56) References Cited

U.S. PATENT DOCUMENTS

| | | | |
|---|---|---|---|
| 5,046,338 A | 9/1991 | Luthi | |
| 5,208,162 A | 5/1993 | Osborne et al. | |
| 5,455,475 A * | 10/1995 | Josse et al. | 310/316.01 |
| 5,646,338 A | 7/1997 | Mercusot et al. | |
| 5,852,229 A | 12/1998 | Josse et al. | |
| 6,030,917 A | 2/2000 | Weinberg et al. | |
| 6,247,354 B1 * | 6/2001 | Vig et al. | 73/54.41 |
| 6,490,927 B2 | 12/2002 | Braunling et al. | |
| 6,823,736 B1 | 11/2004 | Brock et al. | |
| 6,915,242 B2 | 7/2005 | Ghaoud et al. | |
| 7,043,969 B2 | 5/2006 | Matsiev et al. | |
| 7,290,450 B2 | 11/2007 | Brown et al. | |
| 7,334,452 B2 | 2/2008 | Matsiev et al. | |
| 7,598,723 B2 * | 10/2009 | Gaillard et al. | 324/76.42 |
| 7,671,511 B2 * | 3/2010 | Battiston | 310/316.01 |
| 7,866,211 B2 | 1/2011 | Brown | |
| 2003/0121338 A1 | 7/2003 | Yates | |
| 2006/0037399 A1 | 2/2006 | Brown | |
| 2007/0199379 A1 | 8/2007 | Wolf et al. | |
| 2008/0184800 A1 | 8/2008 | Jacobsen et al. | |
| 2008/0314150 A1 | 12/2008 | Wolf et al. | |
| 2009/0249521 A1 * | 10/2009 | Dazzi et al. | 850/33 |

OTHER PUBLICATIONS

PCT/US2010/039108, PCT International Search Report, Form PCT/ISA/210, dated Oct. 11, 2011, 4 pgs.

PCT/US2010/039108, PCT Written Opinion of the International Searching Authority, Form PCT/ISA/237, dated Oct. 11, 2011, 6 pgs.

Hungarian Search Report mailed Jul. 25, 2013 in corresponding Singapore Application No. 201108872-1, 7 pp.

Hungarian Examination Report mailed Jul. 25, 2013 in corresponding Singapore Application No. 201108872-1, 6 pp.

\* cited by examiner

Mechanical Oscillator with Piezo-Electric Transducer

Hardware for Data Capture and Analysis in the Frequency Domain

Frequency Domain Result via FFT over the Full Spectrum

Full Spectrum

Frequency Domain Result via FFT in the Vicinity of the Mechanical Oscillator Resonance

Near Resonance

FFT Derived Response in the Vicinity of the Mechanical Oscillator Resonance

Search range restricted to the frequency range defined by Δf

FIG. 4b

Including FFT Derived Power Response in the Vicinity of the Mechanical Oscillator Resonance Frequency a Curve Fit Representing a Simple Harmonic Oscillator

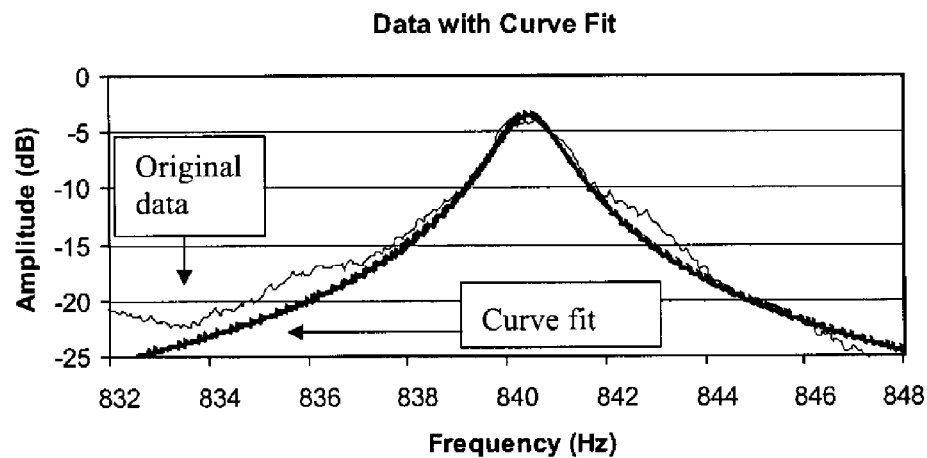

Equation to fit: (in dB space)
$$\frac{a}{b + (f-f_0)^2}$$

$$Q = f_0/(2*\sqrt{b})$$

where a (Amplitude) and b are free parameters used in the curve fitting process $f_0$ = the resonance frequency determined by the curve fitting Q = the quality factor = $f_0/(f_2-f_1)$ where $f_1$, $f_2$ are the half power points $f_1$, $f_2$: $b+(f_1-f_0)2 = \sqrt{b}$ and $b+(f_2-f_0)2 = \sqrt{b}$ f = the frequency parameter

FIG. 4c
Algorithm for Determining the Excitation Frequencies around the Resonance 1) Start with Estimated Primary Frequency (Hz) and Estimated Q Value (EstF$_0$ and EstQ)

2) Compute $\Delta F = \dfrac{EstF_0}{EstQ}$

3) Collect signal at 5 frequencies: EstF$_0$, EstF$_0 \pm \frac{1}{4}\Delta F$, EstF$_0 \pm \frac{1}{2}\Delta F$ 4) Loop: Remove any data points that is less than 10 % of maximum signal 5) Fit data (frequency and power which is square of signal) with $\dfrac{a}{b+(f-f_0)^2}$ 6) Compute $F_0 = f_0$, $F_1 = f_0 - \sqrt{b}$, $F_2 = f_0 + \sqrt{b}$ 7) If there is no data point between $F_0 - \dfrac{(F_0 - F_1)}{8}$ and $F_0 + \dfrac{(F_2 - F_0)}{8}$, set *next frequency* to $F_0$ and go to CollectNextPoint.

8) If there is no data point between $F_0 - \dfrac{(F_0 - F_1)}{8}$ and $F_0 - \dfrac{(F_0 - F_1)}{4}$, set *next frequency* to $F_0 - \dfrac{3(F_0 - F_1)}{16}$ and go to CollectNextPoint.

9) If there is no data point between $F_0 + \dfrac{(F_2 - F_0)}{8}$ and $F_0 + \dfrac{(F_2 - F_0)}{4}$, set *next frequency* to $F_0 + \dfrac{3(F_2 - F_0)}{16}$ and go to CollectNextPoint.

10) If there is no data point between $F_0 - \dfrac{(F_0 - F_1)}{4}$ and $F_0 - \dfrac{(F_0 - F_1)}{2}$, set *next frequency* to $F_0 - \dfrac{3(F_0 - F_1)}{8}$ and go to CollectNextPoint.

11) If there is no data point between $F_0 + \dfrac{(F_2 - F_0)}{4}$ and $F_0 + \dfrac{(F_2 - F_0)}{2}$, set *next frequency* to $F_0 + \dfrac{3(F_2 - F_0)}{8}$ and go to CollectNextPoint.

12) If there is no data point between $F_0 - \dfrac{(F_0 - F_1)}{2}$ and $F_1$, set *next frequency* to $F_0 - \dfrac{3(F_0 - F_1)}{4}$ and go to CollectNextPoint.

13) If there is no data point between $F_0 + \dfrac{(F_2 - F_0)}{2}$ and $F_2$, set *next frequency* to $F_0 + \dfrac{3(F_2 - F_0)}{4}$ and go to CollectNextPoint.

14) CollectNextPoint: Stop if *next frequency* is not set
15) Collect data at *next frequency*
16) Stop if number of data points is equal to or larger than Max TD Pts
17) Go to Loop

Graphical Description of Frequencies Selected for Excitation

The number at each point indicates the order in which the algorithm selected the excitation frequency.

Hardware for Time Domain Data Capture

Time Domain Excitation Tone Burst

Time Domain Response to Tone Burst

Frequency Sweep Maps out a portion of the Frequency Response Immediately Around Resonance

FIG. 8

Time Domain Signal and Parameters Used to Compute the Resonance Parameters Using the Ring-Down embodiment

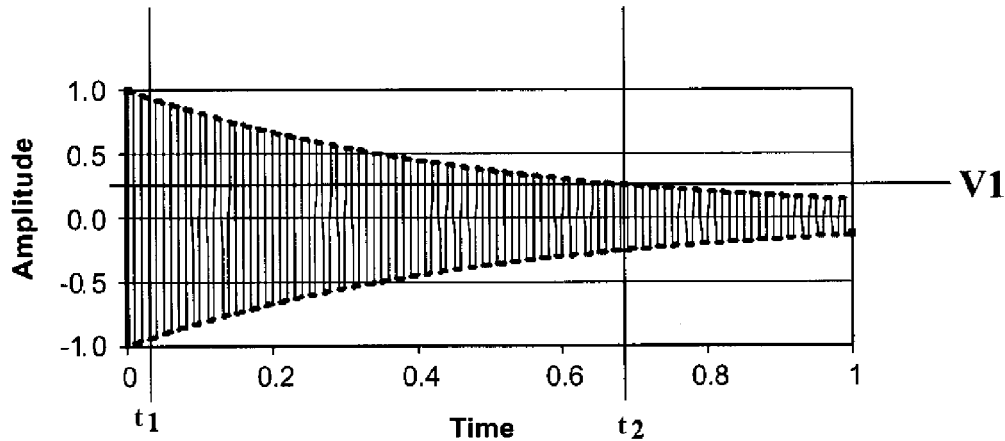

Example Ringdown After Excitation

- t1 = fixed delay after excitation stops prior to data collection to minimize aberrations from the excitation
- "Ringdown min voltages": V1 = voltage must be above this level for cycle to be considered as an acceptable time domain signal
- T2 = time at which V1 occurs
- Minium number of ring-down cycles between t1 and t2 for signal to be considered as an acceptable time domain Comparison of Resonance Frequency Computed by Frequency vs FFT Comparison of Resonance Q Computed by Frequency vs FFT Example of Computing RMS Results to Compute Q from Ringdown Expanded Detail for Data in Figure 10a Comparison of Resonance Frequency Computed by Ring-down vs FFT Comparison of Resonance Q Computed by Ring-down vs FFT

DETERMINING THE RESONANCE PARAMETERS FOR MECHANICAL OSCILLATORS

This application claims the benefit of U.S. Provisional Application 61/269,329 filed Jun. 23, 2009.

BACKGROUND OF THE INVENTION

The present invention relates to mechanical oscillators for the measurement of corrosion and/or deposition. In particular, the invention relates to the determination of the resonance parameters of a mechanical oscillator in the presence of noise.

There is prior art on the use of the resonance parameters of mechanical oscillators to measure corrosion and/or deposition. To determine small changes in these corrosion and/or deposition parameters, it is necessary to reliably measure small variations of the resonance parameters. However, noise often compromises the consistency in determining resonance parameters. The prior art does not disclose the determination of the resonance parameters in the presence of noise.

SUMMARY OF THE INVENTION

The prior art describes the application of mechanical oscillators for the measurement of corrosion and/or deposition. Mechanical oscillators employ the use of resonance parameters, frequency and the quality factor Q, for the measurement of corrosion or deposition. However, the prior art does not consider the required precision for measuring frequency or Q in the presence of noise to make these measurements. In particular, the ability of the mechanical oscillator to measure small amounts of metal loss or deposition is not only dependent upon the mechanical design but is limited by the precision in determining the resonance frequency and Q. The present invention discloses methods for measuring these resonance parameters with a high precision in the presence of noise. This degree of precision is required to maximize the utility of these devices as sensitive probes for corrosion and deposition (fouling) measurement.

The present invention includes three embodiments for determining resonance parameters: Fast Fourier Transform (FFT) (passive method); frequency sweep (time domain active method); and ring-down (time domain active method). All of the embodiments described herein employ curve fitting consistent with modeling the mechanical oscillator as a simple harmonic oscillator. This curve fitting procedure, combined with averaging and utilizing signal processing parameters to mitigate noise effects, adds considerable precision in measuring resonance parameters.

BRIEF DESCRIPTION OF THE DRAWINGS

FIG. 4b shows the FFT Derived Response in the Vicinity of the Mechanical Oscillator Resonance Frequency Including a Curve Fit Representing a Simple Harmonic Oscillator FIG. 4c presents the algorithm for selecting the electrical excitation frequencies for the time domain methods.

FIG. 6b shows the response of the mechanical oscillator to the applied tone burst signal of FIG. 6a.

FIG. 8 provides the definitions of the time domain ring-down signal.

BACKGROUND OF THE INVENTION

Figure 1:
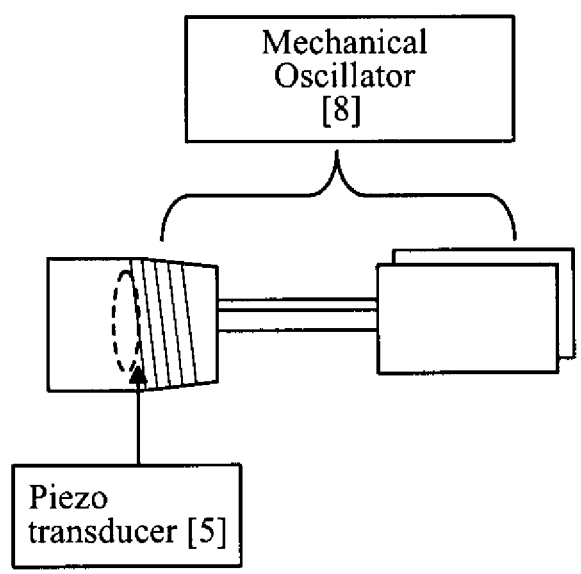
FIG. 1 depicts a mechanical oscillator with a peizo-electric transducer.

Prior art has disclosed and described the application of mechanical oscillators for: measuring fouling deposition; measuring metal loss; and service fluid properties such as density or viscosity. The ability to measure these parameters is linked to the precision and accuracy of measuring the resonance parameters of Q (the quality factor) and the resonance frequency of the mechanical oscillator. The measurement of these resonance parameters may be compromised by the presence of noise. In some cases, the noise may be the inherent measurement reproducibility caused by limitations of the electrical instrumentation. In other cases, noise may be introduced by the environmental effects presented to the mechanical oscillator. These variations are caused by changes in the service environment surrounding the mechanical oscillator. Examples of environmental variables include changes in service fluid density, viscosity, temperature, flow, pressure. For applications directed at measuring service fluid properties (such as viscosity), the prior art identifies algorithms to account for changes in temperature and/or density that occur from a base case calibration. Even for the case where the aforementioned environmental parameters are invariant, fluid flow provides random excitation and relaxation to the mechanical oscillator such as the tines of a tuning fork. These successive excitations and relaxations randomly impact the tines with random phase. This randomness can cause very minor variations in the apparent resonance frequency that would not be observed in the absence of fluid flow. The result is added noise to the measurement of the resonance parameters.

What is absent in the prior art is a methodology to accurately account for the following two separate situations: 1) random variations that occur during the measurement of resonance parameters; and 2) biased drifts in the resonance parameters that smear their determination if the measurement time is sufficiently long to permit a significant drift of the resonance parameters.

The prior art documents the ability to apply signal averaging as a means to reduce variability from noise. Although signal averaging is beneficial and is included in the strategy of this invention, it has negative impact of introducing additional noise. Additional noise is introduced because averaging inherently requires an increase in the time required to collect the data. In cases where the noise is correlated with a process variable (such as a biased increase in temperature), the measurement of the resonance parameters will also be biased. This invention discloses embodiments that enable a reduction of the measurement time to reduce this averaging bias.

The prior art also discloses the possibility of using active excitation frequency sweep methods for measuring the resonance parameters. However, those methods do not consider the presence of noise and can be tedious (time consuming) since they require that the excitation frequency precisely match the resonance frequency. Such methods typically define resonance as the excitation frequency causing maximum oscillator amplitude or minimum excitation current draw. The instant invention does not require that the electrical excitation frequency match the actual resonance of the mechanical oscillator.

DESCRIPTION OF THE PREFERRED EMBODIMENT

Mechanical oscillators have been used for the measurement of corrosion and/or deposition. However, the accuracy of the measurements depends on the presence of noise from the medium, such as flow, viscosity, and temperature. The present invention reduces the noise impact of measuring the resonance parameters with three embodiments. One of the embodiments uses fast fourier transform (FFT) and the other two use time domain (frequency sweep and ring-down) techniques. The ability to determine the resonance parameters in the presence of noise also enables their automated determination. Accordingly, it is then able to fit the mechanical oscillator with a hardware/software system that enables automated successive determination of the resonance parameters. These embodiments are described below.

Frequency Domain FFT Method

Figure 2:
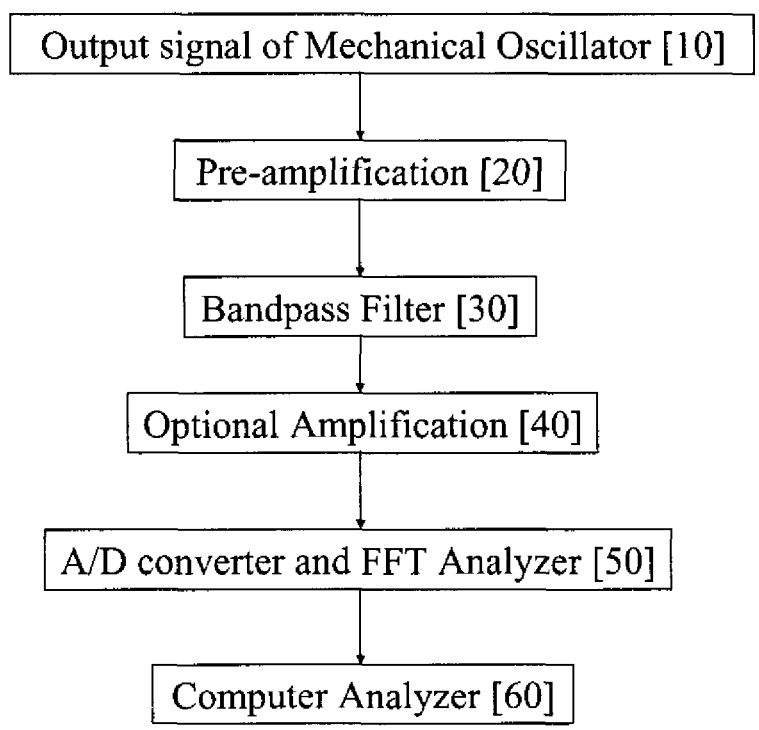
FIG. 2 shows the hardware arrangement for data capture and analysis in the frequency domain.

The assumption for this method is that the flow of the service fluid provides the mechanical excitation of the oscillator. As such, this FFT approach is said to be operating passively since there is no external electrical excitation to the mechanical oscillator. As shown in FIG. 1, the passive signal is provided by transducer [5] attached to the mechanical oscillator [8] that converts the mechanical energy to an electrical signal. The selected transducer type (e.g. piezo, inductive, displacement sensor etc.) has little impact on the methodology described in this invention. An FFT is computed over the desired frequency range using a pre-selected frequency resolution. Filtering in the time and frequency domains combined with frequency domain averaging provide considerable smoothing of the resonance peak. Although increasing resolution and averaging may be directionally beneficial, each has the undesirable effect of increasing the data collection time. Increasing the data collection time increases frequency domain smearing for systems where the resonance parameters are not time invariant. FIG. 2 shows the typical hardware used for the frequency domain FFT-derived response. The electrical output signal [10] of the mechanical oscillator typically needs amplification prior to subsequent signal analysis. In the case where a piezo device is used to transform the mechanical energy into electrical energy, preamplifier [20] is typically a charge type amplifier. The output of preamplifier [20] will drive some degree of analog filtering. Bandpass filter [30] preceding the analog to digital (A/D) [50] conversion for computing the FFT is a well-known method for reducing noise that is not in the immediate vicinity of the resonance frequency. Bandpass filtering not only provides relief from low frequency noise (such as 60 Hz interference) but also provides high pass anti-aliasing filter required prior to the analog to digital conversion. Depending on the particular hardware, an optional amplifier [40] might be required ahead of the FFT analyzer [50] which includes an analog to digital (A/D) converter. After A/D conversion, additional digital filtering can supplement noise suppression available in computer processor [60]. However, none of these filters will have the capability to suppress noise in the immediate vicinity of the mechanical resonance. Algorithms implemented by the computer [60] enable the curve fitting and computation of the resonance parameters.

Increasing the number of averages increases the required data collection time in proportion to the number of averages. In cases where very fine frequency resolution is required, the FFT resolution step size must be reduced. This action also increases the data collection time in direct proportion to the step size reduction.

Figure 3A:
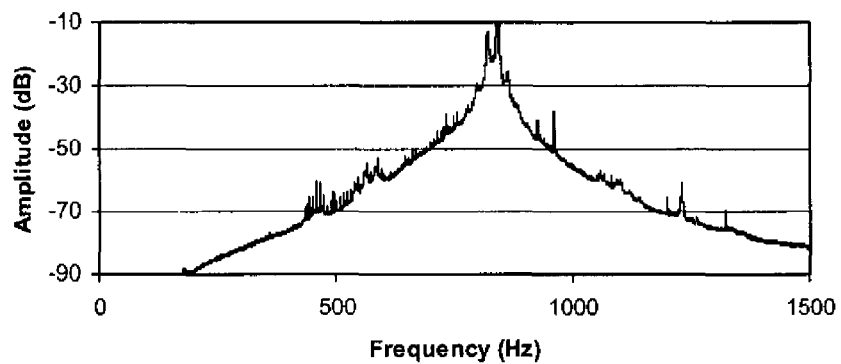
FIG. 3a shows Frequency Domain Result via FFT over the Full Spectrum.

FIG. 3a shows an example of the FFT-derived frequency domain spectrum. These data were collected in a stirred reactor where the liquid temperature was 550° F. and the stirring speed was 300 rpm. For this case, the FFT resolution step size is 0.05 Hz and 400 frequency domain averages were used to make the average shown in FIG. 3a. The resolution step size of 0.05 Hz dictates that the time required for collection of a single FFT spectrum is 20 seconds (1/0.05). Therefore, 2000 seconds are required to collect sufficient spectra for 100 averages. An analog bandpass filter with a passband range of 820-850 Hz was employed as shown in FIG. 2. Although the filter frequency roll-off is 6 dB/octave, it was not sufficient to suppress several extraneous amplitude peaks that are not directly related to the fundamental mechanical resonance.

Figure 3B:
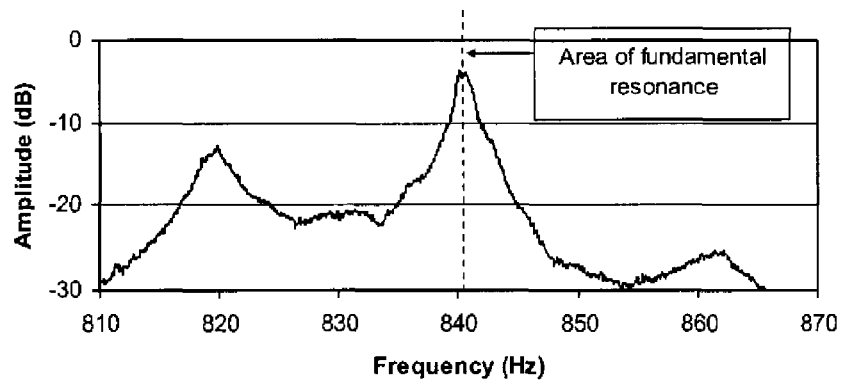
FIG. 3b shows the Frequency Domain Result via FFT in the vicinity of the resonance of the mechanical oscillator.
Figure 4A:
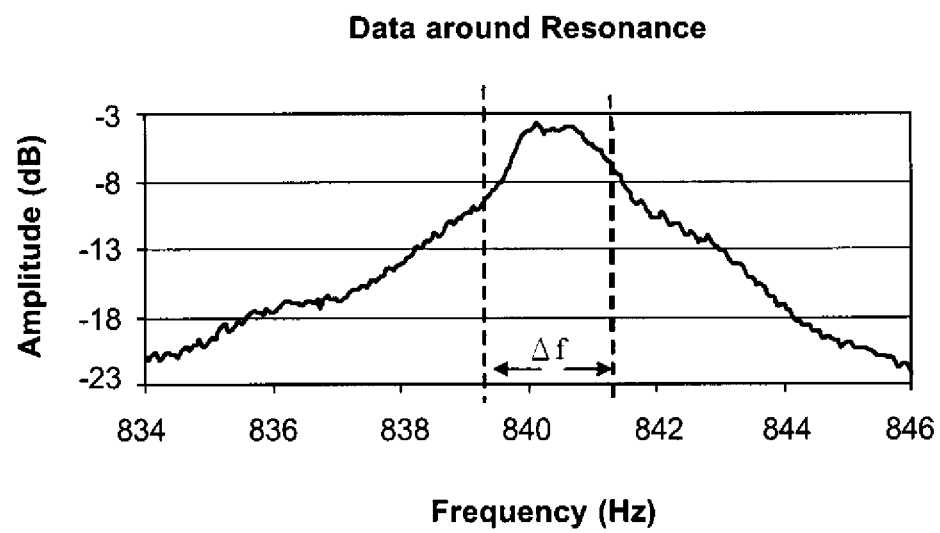
FIG. 4a shows the FFT Derived Response in the Vicinity of the Mechanical Oscillator Resonance Frequency.

FIG. 3b presents the spectrum of FIG. 3a in more detail around the resonance frequency of the mechanical oscillator. The resonance frequency of the mechanical oscillator in this environment was independently determined using the time domain methods subsequently described that provide considerably reduced noise. In order to prevent other extraneous high amplitude peaks to be mistaken for the resonance (such as the one at 820 Hz in FIG. 3b) a bounded search range is specified encompassing the frequency of the most probable resonance. For mechanical oscillators with Q's in the range of 200-4000 and resonance frequencies between 500-1500 Hz, experience indicates that a search range 2-20 Hz as being satisfactory. The search range is centered on the most recently determined or estimated resonance frequency. The search range parameters ($\Delta f$) for this example are shown in FIG. 4a. As can be observed, the environmental conditions associated with the results presented in FIG. 3b show that the exact resonance frequency cannot be accurately determined by inspection. Although those data shown in FIG. 4a do indicate that the resonance appears to be in the vicinity of 840-842 Hz, it is not clear if the maximum amplitude is actually the true resonance. Algorithmically, one could use the rule to select the frequency corresponding to the peak amplitude in that range. However, that rule is problematic when it is desired to make a measurement that will not be dependent upon very small shifts in the frequency response at the resonance that are attributable to noise. Because of variability of flow noise, the frequency corresponding to the peak amplitude in the 840-842 Hz range is variable.

Repeated testing at the conditions that created the FIG. 3b results shows that the approximate resonance range is exceptionally consistent but the spectral details within the 840-842 Hz range are variable. That observation motivates the selection of resonance frequency by applying a curve fit to the averaged FFT spectra. The variability in selecting the peak amplitude can be minimized by using the fitted curve to estimate the resonance parameters rather than making that selection from the actual the data. FIG. 4b shows the result of using a curve fit based on the harmonic oscillator (equations shown FIG. 4b). The resonance frequency is determined by finding the maximum amplitude of the curve fit. For the 2$^{nd}$ order system, the parameters a (Amplitude), $f_o$, and b are free parameters available for a best-fit adjustment. In the FIG. 4b example, a best fit is obtained by using commonly available search algorithms to minimize the error between the average spectral data and the harmonic oscillator fit. Since the parameters of interest are defined at resonance, the curve is fit only to data within 5 dB of the maximum spectral amplitude. As shown in FIG. 4b, the resonance quality factor Q is computed by the computation of the 3 dB (half power) points of the harmonic oscillator curve.

Time Domain Methods

Figure 5:
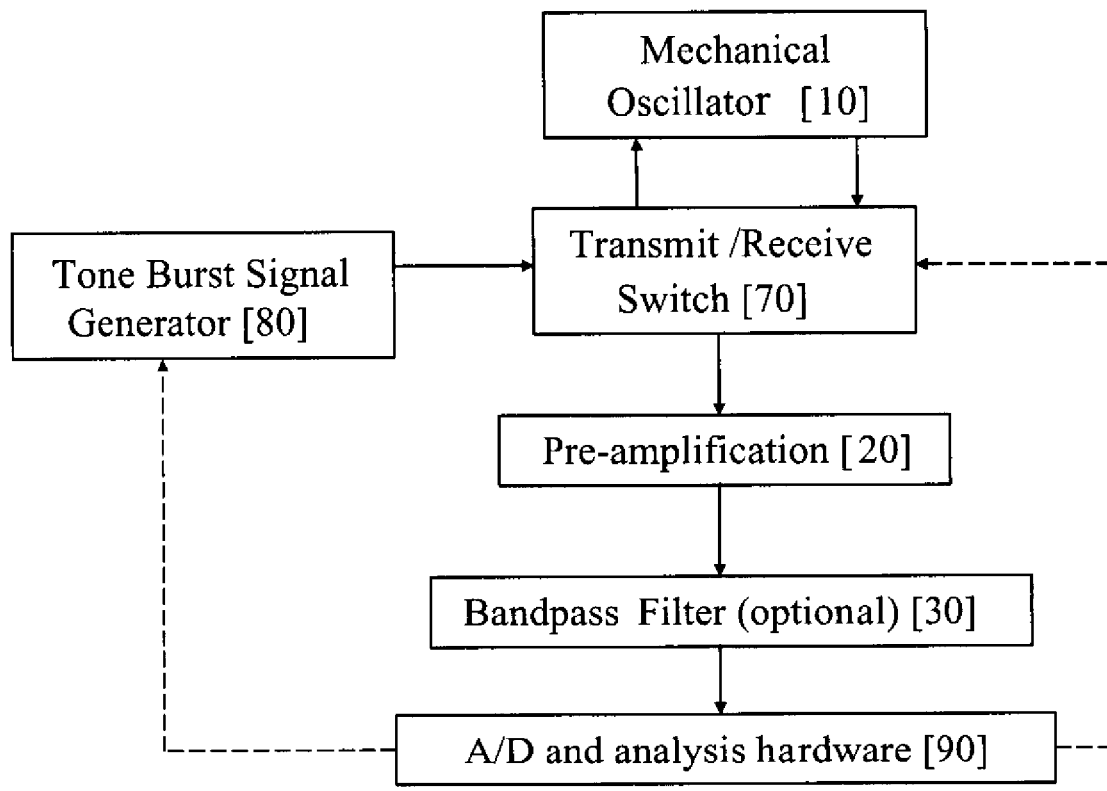
FIG. 5 shows the hardware arrangement for data capture and analysis in the time domain.

In contrast to the previously described FFT method, the time domain methods require the application of an external electrical excitation. The hardware for the time domain methods, including the electrical excitation, is shown in FIG. 5. The primary hardware differences between the time domain and the previously described frequency domain set-up are the added transmit/receive (T/R) switch [70] and the required signal generator [60]. Moreover, the time domain method does not use FFT hardware nor does it compute the full frequency response. Signal generator [80] provides the electrical excitation to the transducer (FIG. 2, item [5]) in the mechanical oscillator. T/R switch [70] connects the mechanical oscillator to the signal generator while the tone burst is active and changes the connection of the mechanical oscillator to the A/D and analysis hardware [90] when the tone burst signal is off. In some embodiments it is possible to forgo a T/R switch.

The Frequency Sweep Method and Ring-Down Method are considered time domain methods since there is no explicit computation or measurement of the full frequency response. Both methods employ averaging by computing each data point in the resonance calculation several times at the same frequency. The primary advantage of the time domain methods compared to the FFT method is their improved stability and precision. However, this advantage is only maintained if the mechanical oscillator can be driven at a sufficient level so that its forced excitation signal is greater than the passive signal, if any.

Figure 4D:
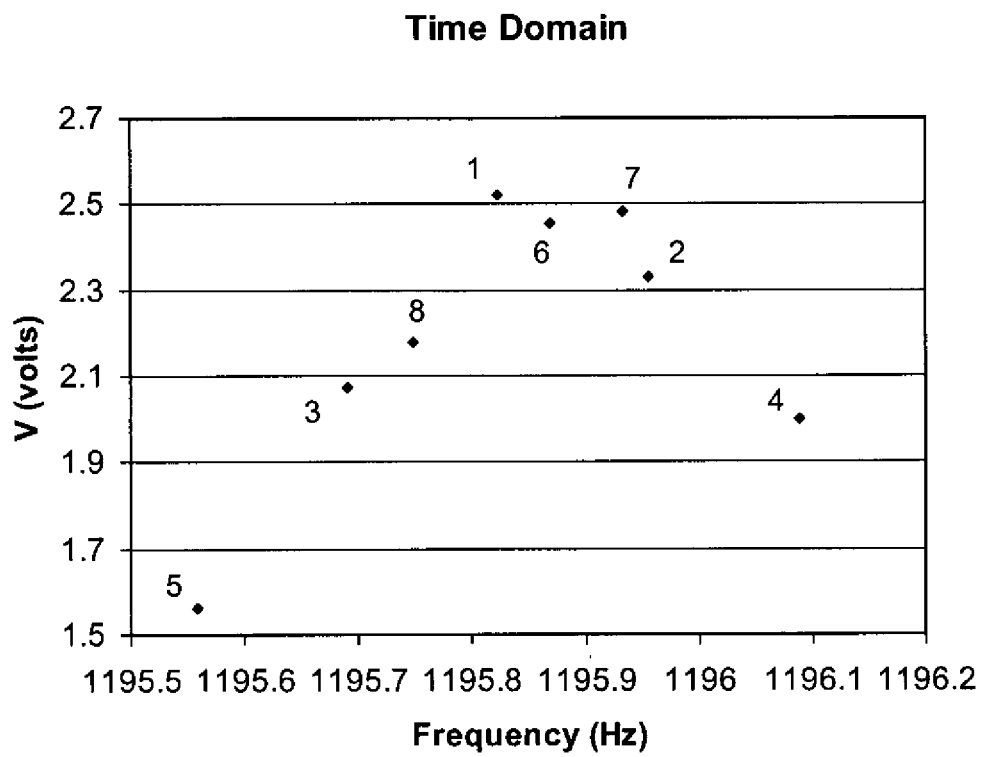
FIG. 4d illustrates the order for selecting the frequencies for the time domain method algorithm outlined in FIG. 4c.

One approach for selecting the frequencies of the frequency sweep method is to excite the mechanical oscillator at equally spaced successively higher frequencies. Although this approach will generate a satisfactory frequency response, it may require the use of many frequencies. Consequently, the time to generate the frequency response may be unacceptable in the presence of variable noise. The algorithm shown in FIGS. 4c and 4d is an approach to significantly reduce the number of frequencies required for the frequency sweep method.

Recursive application of the methods described in FIGS. 3 and 4a,4b,4c enables successive and automated computation of the resonance parameters. This capability enables the mechanical oscillator to be used in applications where continual and unattended computations of the resonance parameters are required. Typically, the frequency range to search for the new resonance frequency will be centered around the most recently determined resonance frequency. Examples of applications benefiting from successive, automated measurements include corrosion and fouling monitoring.

In some embodiments, it may be desirable for the time domain methods to operate using a lock-in amplifier. Lock-in amplifiers are well-known devices where the bandpass frequency of the receiving electronics is narrowly matched to electronic excitation frequency. Although lock-in amplifiers may be most advantageous for low Q devices where there is high background noise, the benefit should be assessed for mechanical oscillators which are typically high Q.

Figure 6A:
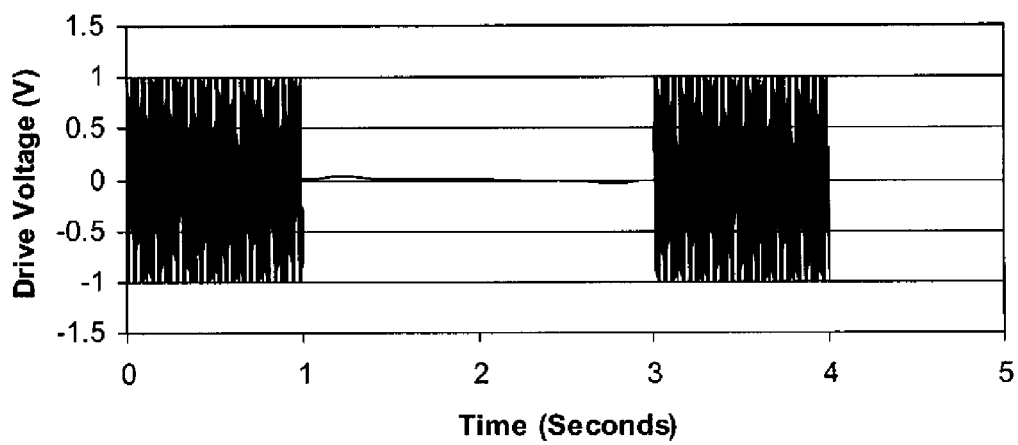
FIG. 6a shows a representative tone burst electrical signal used to drive the mechanical oscillator.

The electrical excitation may be a tone burst signal as shown in FIG. 6a. The tone burst in this example consists of a sine wave signal whose frequency is in the vicinity of resonance of the mechanical oscillator. The amplitude and length of the burst signal should be sufficient to activate the mechanical oscillator to a level greater than provided by the flow of the service fluid. For the frequency and Q ranges described for FFT operation, a typical duration range for the burst signal is 100-5000 cycles with an off period of 0.5 to 10 seconds. Although the burst signal in this example is sine wave, alternatively, it can be a square wave or a series of pulses. A benefit of the time domain method is that erroneous resonances (such as the peak in the FIG. 3b FFT at 820 Hz) cannot be energized.

Figure 6B:
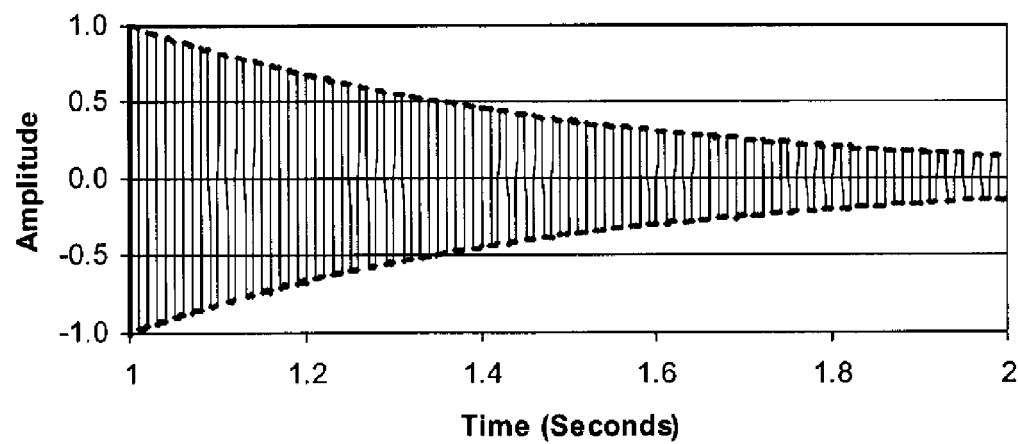

In addition to the tone burst generator [80], time domain operation may include a transmit/receive switch (T/R switch) [70] as shown in FIG. 5. The purpose of the T/R switch is to change the connection of the transducer in the mechanical oscillator to either the tone burst signal generator or to the receiving circuit. A T/R switch would not be required in applications where the hardware receiving circuit can accommodate the strong signal produced during the transmit cycle. The actual signal used by the time domain method occurs after the tone burst stops (denoted as the ringdown signal of FIG. 6b). This ringdown signal has the frequency equal to the resonance of mechanical oscillator. Its amplitude is a function of the frequency of the burst signal. The amplitude is greatest when the frequency of the burst signal is equal to the resonance frequency of the mechanical oscillator. The decay time of the ringdown signal is related to the Q of the mechanical oscillator: higher Q correlating to a longer ringdown signal.

The computer [90] serves two purposes: combined with the A/D converter, it enables manipulation of the data in the frequency sweep and ringdown methods. Secondly, the computer serves as a controller for the tone burst generator [80] and the T/R switch [70].

Figure 7:
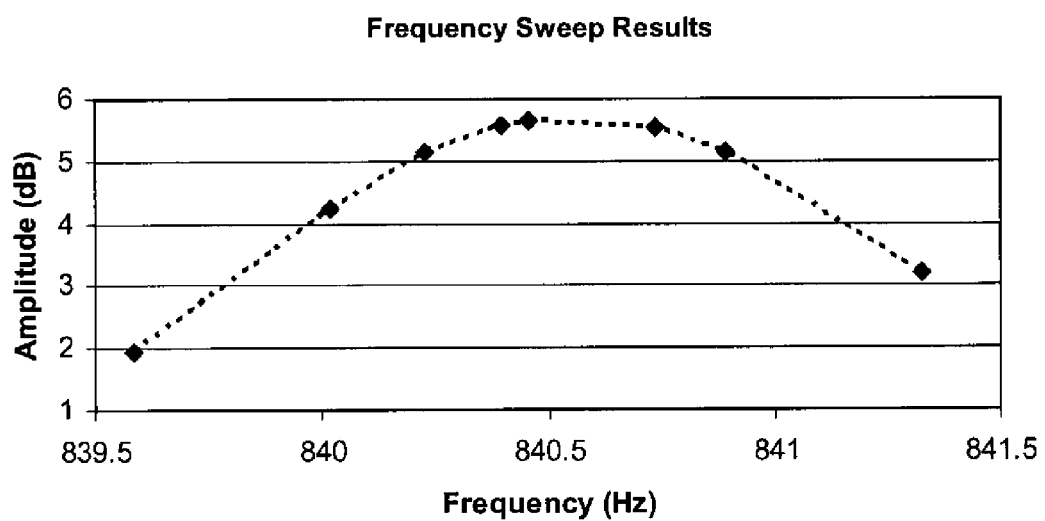
FIG. 7 shows the result of the frequency sweep in the vicinity of the resonance.

The frequency sweep method does map out a portion of the frequency response function immediately around resonance, as shown in FIG. 7. This measurement is made by driving the mechanical oscillator at specific frequencies near resonance. By operating in a transceive mode, the amplitude at the drive frequency is measured. The measurement is made by computing the root mean square (rms) signal level over a time interval that initiates after a fixed time ($t_1$ in FIG. 8) after the excitation terminates. The frequency scale for FIG. 8 is the excitation frequency. The interval for computing the rms signal level ends at time $t_2$ in FIG. 8. Time $t_2$ is selected so that the amplitude of the ringdown signal is not significantly impacted by any background noise. Additional drive frequencies are algorithmically selected to map out the oscillator response immediately around the resonance frequency (FIG. 7). The time period $t_1$ to $t_2$ remains approximately constant for all applied frequencies and represents a fixed number of whole cycles.

The first applied frequency is either the initial resonance estimate or the previously determined measured resonance frequency. This frequency is denoted below as $f_o$. Subsequent frequencies are alternatively selected higher and lower than this frequency to map out amplitudes in the vicinity of the resonance. This algorithm deploys a search routine using the estimated or previously measured Q to determine the frequency step size. Step sizes around this estimated resonance frequency or previously measured resonance frequency are determined as follows:

$$\Delta f = f_o / Q$$

Where:
$\Delta f$=frequency step parameter
$f_o$=estimated resonance frequency or previously measured resonance frequency
Q=estimated quality factor or previously measured quality factor
Step sizes around the $f_o$ frequency are determined as follows:

$$\pm \Delta f/4; \pm \Delta f/2$$

After the applying the electrical excitation at the five frequencies identified above, the corresponding rms amplitude at each frequency is determined. Using these amplitudes and frequencies, the harmonic oscillator curve fit described previously is applied to the data to determine resonance frequency and Q. If the curve fit does not satisfy the conditions listed in FIG. 3c, additional drive frequencies are added to generate more points for the curve fitting process. With this algorithm, it is not necessary to actually drive the oscillator at its resonance frequency to determine the exact resonance or Q. The resonance frequency is determined by the curve fit.

The frequency sweep method is more noise immune than the FFT method in cases where the assumption of exciting the mechanical oscillator more than the flow excitation is satisfied. FIG. 9 compares results from the FFT method to the frequency sweep method. This example is from a 1 liter reactor with a stirrer operating at approximately 300 rpm. The temperature is fixed at 550° F. so the primary noise is from the fluid flow by stirring. The FIG. 9 results show a much reduced variability for the frequency sweep method compared to the FFT method. The FFT method with a resolution of 0.05 Hz and 400 averages requires 8000 seconds to compute each resonance frequency estimate. In contrast, the frequency sweep method applies 10 averages to compute each amplitude plotted in FIG. 8 and can compute a resonance frequency estimate in approximately 300 seconds.

The ring-down approach uses the same data as the frequency sweep method. The drive signal for ring-down is the same tone burst used for the frequency sweep method. This ring-down signal is the same signal used in the frequency sweep method. Similar to the frequency sweep method, the value for $t_2$ (FIG. 8) is selected so that the ring-down signal is not compromised by passive background noise. For the ring-down approach, the frequency is computed by counting the number of zero crossings that occur between $t_1$ and $t_2$. Since the mechanical oscillator vibrates at it resonance frequency, it is not necessary that the drive frequency matches the true resonance frequency. However, the signal to noise ratio benefits when the drive frequency is close to the true resonance frequency.

Using the approaches described above for computing the resonance frequency via ring-down and frequency sweep, data that follow demonstrate that the ring-down approach provides less variability. That observation is attributed to directionally more averaging associated with the ring-down computation than the frequency sweep computation. As described previously, both methods use the same data. For example presented in FIG. 7, eight points are used to define the curve fit for the frequency sweep method. After fitting the curve, the equation in FIG. 6 is used to compute the resonance frequency. In contrast, the ring-down method computes the average frequency measured from each of the ringdowns used in the data for FIG. 7. In FIG. 7 each point is computed from 10 ring-downs. Therefore, the resonance frequency for the ring-down method uses the average of 80 ring-downs to compute the resonance frequency (8 points×10 ring-downs per point).

The value of Q is determined by curve fitting a linear regression to the envelope of the ring-down signal.

$$Q = \frac{4.34 * 2\pi * fo}{D}$$

where $\pi$=3.14159 . . .
D=decay rate (dB/second) as shown in FIGS. 10a/b
$f_o$=resonance frequency (determined by zero crossings)

Figure 10A:
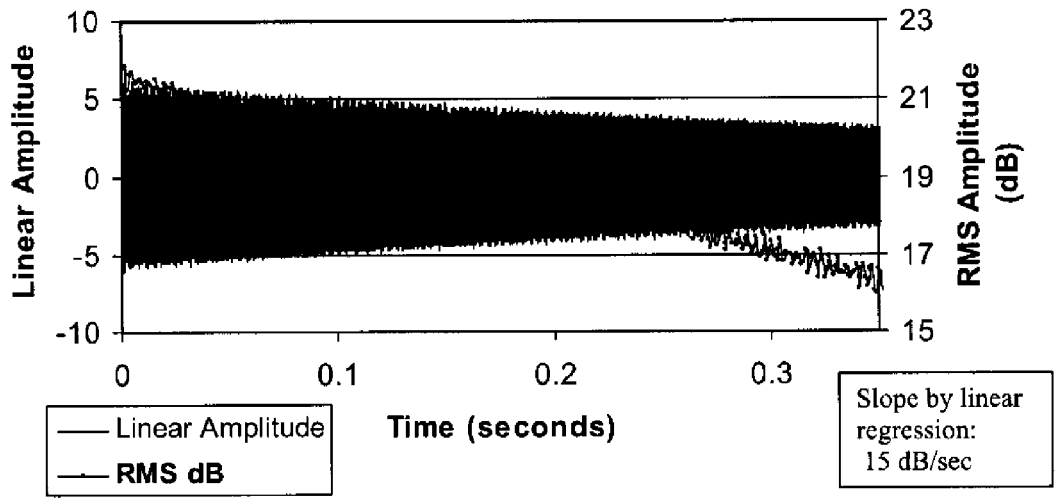
FIG. 10a/b illustrate how the time domain decay parameter, D, is computed.
Figure 10B:
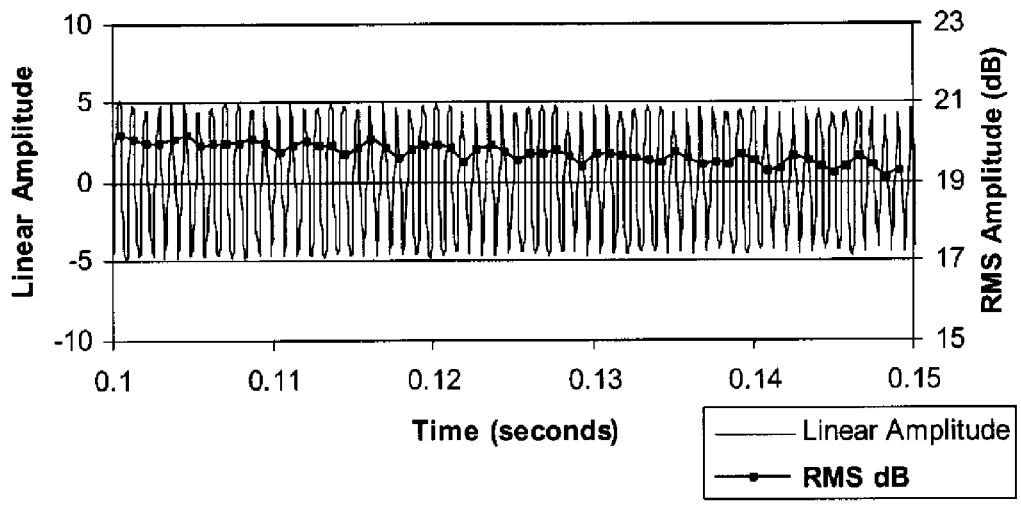

As shown in FIGS. 10a/b, the decay rate parameter D is computed by fitting a linear regression to rms amplitude decibel (dB) data. In this example, the rms amplitude is computed on a per cycle basis, where the start of a cycle is defined as a transition from positive to negative signal in FIGS. 10a/b and the end of the cycle is defined as the last point before the next positive to negative transition. In cases of more signal variability, it can be beneficial to increase the computational time period to several cycles.

Figure 9A:
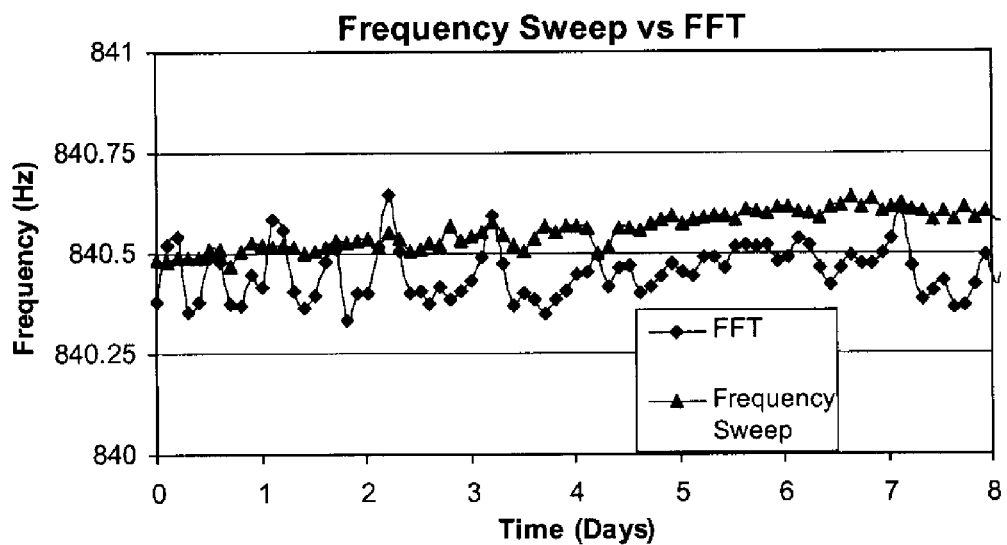
FIGS. 9a/b compare the FFT result with the frequency sweep method: (a) the resonance frequency and (b) the resonance Q.
Figure 9B:
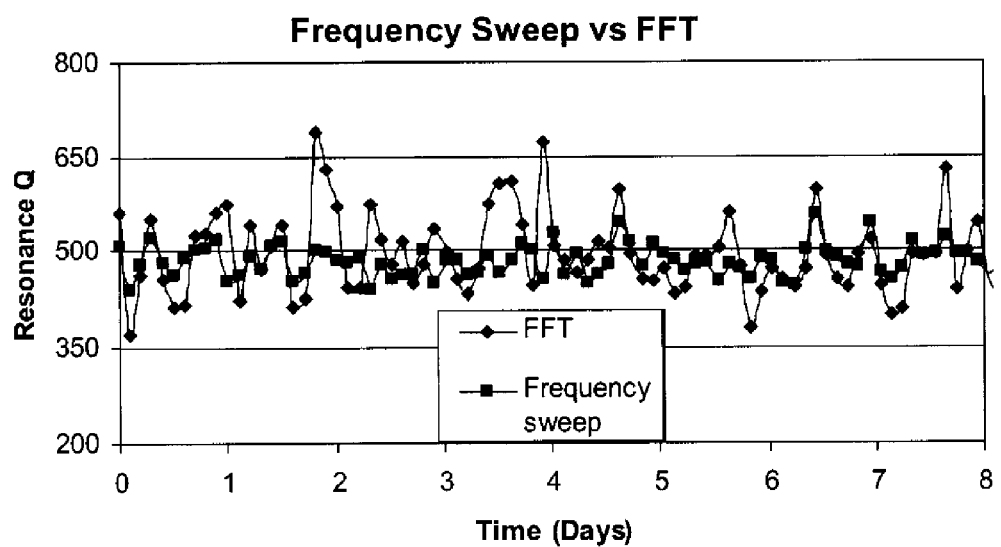
Figure 11A:
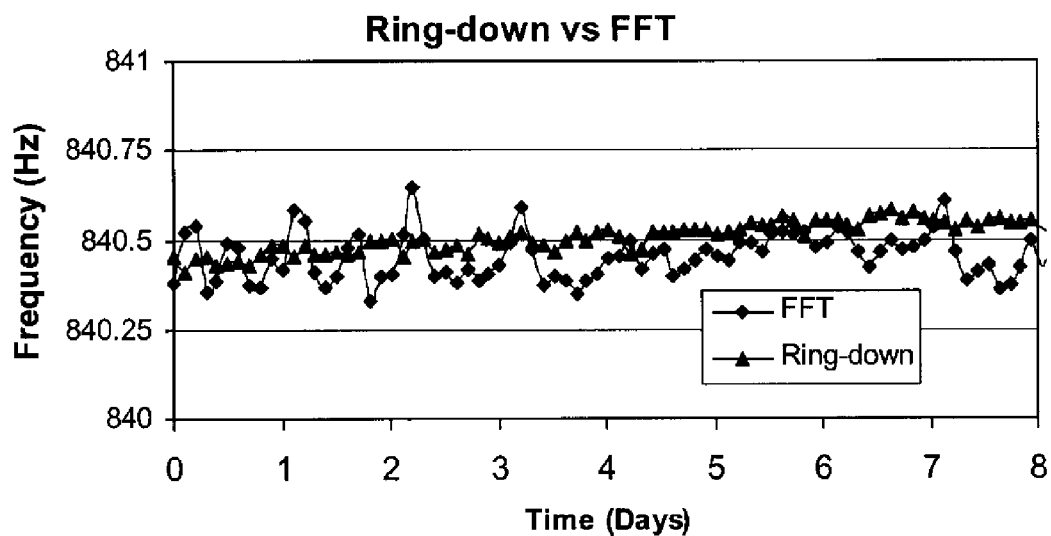
FIGS. 11a/b compare the FFT result with the ring-down method: (a) the resonance frequency and (b) the resonance Q.
Figure 11B:
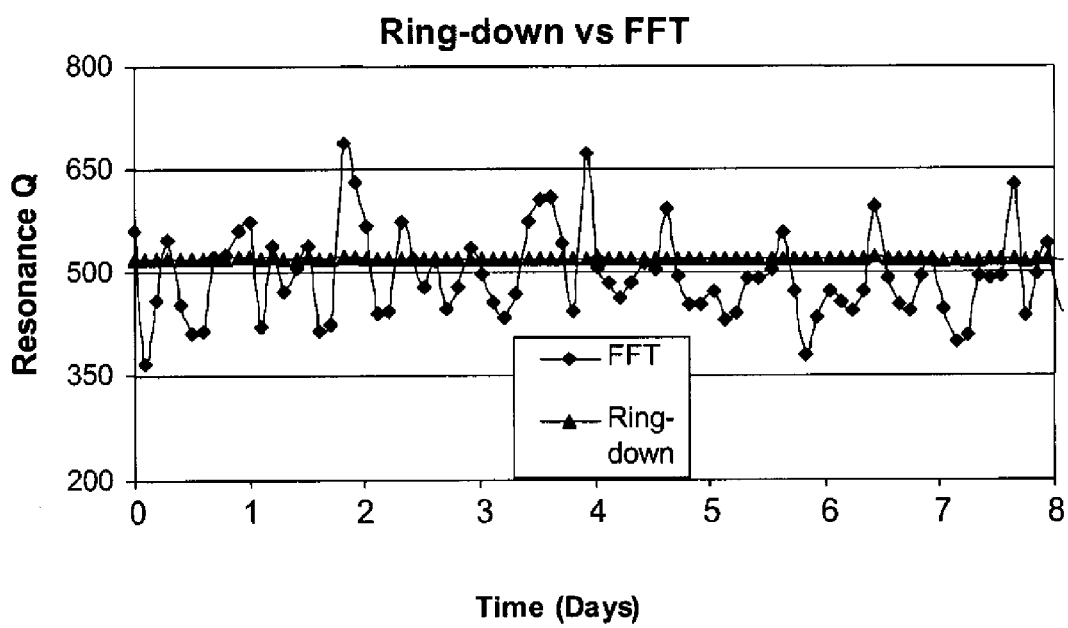

Similar to FIGS. 9a/B, FIGS. 11a/b compare the results of the ring-down method to the FFT method. FIG. 11a compares the resonance frequencies and FIG. 11b compares the resonance Qs. The data for FIGS. 9a/b and 11a/b were all collected at the same time for the same reactor. FIG. 11a/b show a much reduced variability for the ringdown method compared to the FFT method. The ring-down data for FIGS. 11a/b are the same data collected during the same 300 second time period required for the collection of the frequency sweep method.

FIGS. 9a/b and FIGS. 11a/b demonstrate the improved noise immunity for the time domain methods compared to the FFT method for situations where the variability has zero bias. In this case, zero bias implies that the frequency and Q should be stable over the time period of the measurement. To within experimental stability, the data collection conditions for FIGS. 9 and 11 should exhibit a high degree of stability for the resonance conditions of the mechanical oscillator. The reduced data acquisition time for the time domain methods is preferable in situations where factors affecting the resonance parameters may be variable with a non-zero bias. The other advantage of the time domain method is that it provides 2 independent data analysis methods for computing the resonance parameters without increasing the data collection time.

Similar to the frequency domain FFT method, the frequency sweep and ringdown methods are also amenable for successive, recursive, automated implementation. The primary difference for these time domain methods is that the starting frequency for the signal generator [70] is the previously determined resonance frequency Combining Time and Frequency Domain Methods One approach for implementing the time and frequency domain methods described above is to use the previously determined frequency and Q as the starting point for finding the next values. Although this approach is generally reliable for the FFT frequency domain method, there are cases where changes in noise may temporarily compromise the time domain measurement. An example of such a situation is when one or more parameters changes very rapidly during the data collection interval. In such cases, the resulting time domain measurement may be completely erroneous because of varying amplitudes and frequency smearing. This problem can be resolved by using the frequency domain results as the starting point for the next time domain search computation. Although this sort of dual domain data collection may not always be necessary, it can be made available on an as needed basis, Other Frequency Ranges The data shown in FIGS. 9 and 11 are for mechanical tuning fork oscillators with a length scale of a few inches and corresponding resonance frequencies on the order of 1000 Hz and Qs in the range of 200-5000. Data are also available for microcantilevers with length scales on the order of tens to hundreds of microns ($1*10^{-6}$ meters). Typical resonance frequencies for such oscillators are 10-300 KHz, and Q's in the range of 200-500. These tuning forks can operate either with passive or active actuation with the signal collected in the methods mentioned above.

What is claimed is:

1. A method for determining resonance parameters, resonance frequency f and quality factor Q, for a mechanical oscillator in a service fluid environment in the presence of noise produced by the service fluid comprising:
   a) estimating the resonance parameters for a mechanical oscillator in a service fluid environment based on an excitation of the mechanical oscillator by a flow of the service fluid, the estimate of the resonance parameters being determined from the steps of determining a fast Fourier transform of amplitude as a function of frequency, wherein said estimate of the resonance parameters is determined from averaging the fast Fourier transform run multiple times;
   b) exciting the mechanical oscillator in the service fluid environment using a signal generator at one or more excitation frequencies selected based on the estimated resonance parameters, the service fluid environment producing noise that causes an excitation;
   c) determining a response to said exciting of the mechanical oscillator at the one or more excitation frequencies; and
   d) determining f and Q, using a computer, from the response with multiple measurements and curve fitting and averaging.

2. The method of claim 1 wherein the determination of step c) is accomplished with a digital computer.

3. The method of claim 1 wherein f and Q are determined from the steps of terminating the excitation at the one or more excitation frequencies produced by said signal generator so that the amplitude of said oscillator decreases from which amplitude as a function of excitation frequency is determined repeating this step so as to obtain an average value of f and Q.

4. The method of claim 3 wherein f and Q are determine from a frequency sweep signal.

5. The method of claim 1 wherein f and Q are determined from the steps of terminating the excitation at the one or more excitation frequencies produced by said signal generator so that the amplitude of said oscillator decreases, obtaining f from the crossing of the amplitude of zero and Q from the decline of the amplitude, repeating the above steps to obtain an average value for f and Q.

6. The method of claim 5 wherein f and Q are determined from a ringdown signal.

7. The method of claim 1 where the one or more signal generator excitation frequencies are algorithmically selected based on the estimated resonance parameters to minimize the required number of frequencies.

8. The method of claim 1 wherein the signal generator excitation confirms or refutes peaks in the fast Fourier transform as the oscillator resonance.

9. The method of claim 1 applied recursively to determine f and Q as a function of time.

* * * * *